(12) United States Patent
Selig

(10) Patent No.: US 8,449,536 B2
(45) Date of Patent: May 28, 2013

(54) ELECTRODE DEVICE

(75) Inventor: Peter Selig, Hechingen (DE)

(73) Assignee: Erbe Elektromedizin GmbH, Tübingen (DE)

( * ) Notice: Subject to any disclaimer, the term of this patent is extended or adjusted under 35 U.S.C. 154(b) by 779 days.

(21) Appl. No.: 12/374,265

(22) PCT Filed: Jul. 12, 2007

(86) PCT No.: PCT/EP2007/006215
§ 371 (c)(1),
(2), (4) Date: Jan. 16, 2009

(87) PCT Pub. No.: WO2008/009385
PCT Pub. Date: Jan. 24, 2008

(65) Prior Publication Data
US 2009/0281539 A1    Nov. 12, 2009

(30) Foreign Application Priority Data

Jul. 19, 2006   (DE) .......................... 10 2006 033 510
May 2, 2007    (DE) .......................... 10 2007 020 583

(51) Int. Cl.
  *A61B 18/04*   (2006.01)
  *A61B 18/18*   (2006.01)

(52) U.S. Cl.
  USPC .............................................. 606/35; 606/41

(58) Field of Classification Search
  USPC ..................................................... 606/32, 41
  See application file for complete search history.

(56) References Cited

U.S. PATENT DOCUMENTS

| | | | |
|---|---|---|---|
| 4,416,276 A * | 11/1983 | Newton et al. | 606/35 |
| 2005/0159738 A1* | 7/2005 | Visram et al. | 606/34 |
| 2006/0074411 A1* | 4/2006 | Carmel et al. | 606/32 |

FOREIGN PATENT DOCUMENTS

| | | |
|---|---|---|
| CA | 1 219 642 | 3/1987 |
| DE | 32 39 640 | 5/1983 |
| DE | 32 39 640 A1 | 5/1983 |
| DE | 32 06 947 | 9/1983 |
| DE | 32 06 947 A1 | 9/1983 |
| EP | 0 262 888 | 4/1988 |
| EP | 0 390 937 | 11/1994 |
| EP | 1 173 095 | 6/2004 |
| EP | 1 051 949 | 11/2005 |
| JP | 50-9399 U | 1/1975 |
| JP | 58-103445 A | 6/1983 |
| JP | 3-280946 A | 12/1991 |
| JP | 2002-542866 A | 12/2002 |
| WO | WO 00/65993 A1 | 11/2000 |
| WO | WO 2006/041756 | 4/2006 |

OTHER PUBLICATIONS

Intl. Preliminary Report on Patentability and Written Opinion (English Translations) for PCT/EP2007/006215.

* cited by examiner

*Primary Examiner* — Nicholas Lucchesi
*Assistant Examiner* — Weng Lee
(74) *Attorney, Agent, or Firm* — Dickstein Shapiro LLP

(57) ABSTRACT

Neutral electrodes (used for introducing a high frequency treatment current via a skin section of a human or animal body) that include, in addition to known components, at least one measuring electrode spaced from the main electrode, and at least one measuring current generator that is connected to the main electrode and to the measuring electrode generating a high frequency measuring current, which flows between the measuring electrode and the main electrode. The neutral electrodes thus allow for monitoring of the contact of the neutral electrode with the skin and for monitoring of the high frequency current flow and its spatial distribution. This allows for increased safety during use of the neutral electrode for treatment.

13 Claims, 4 Drawing Sheets

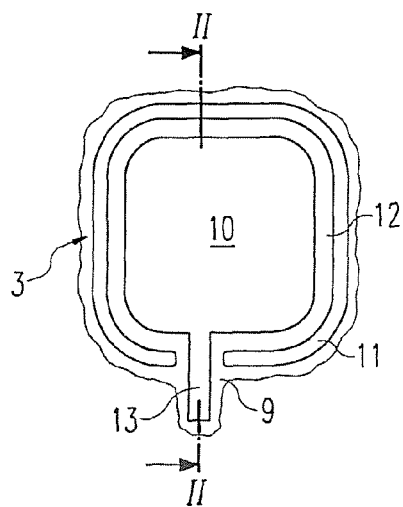
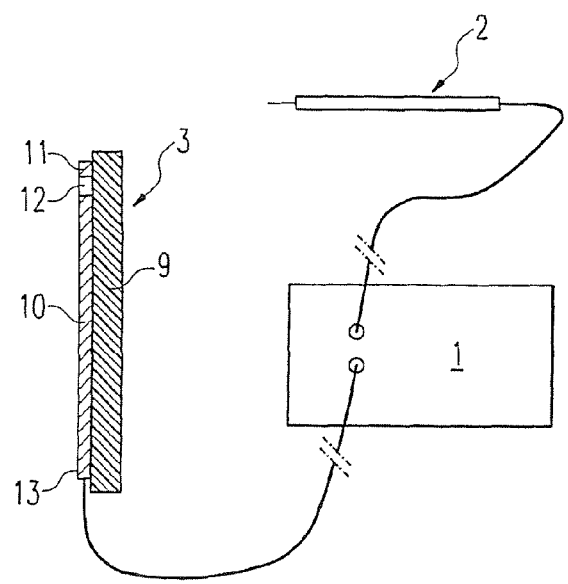
Fig. 1
PRIOR ART
Fig. 2
PRIOR ART
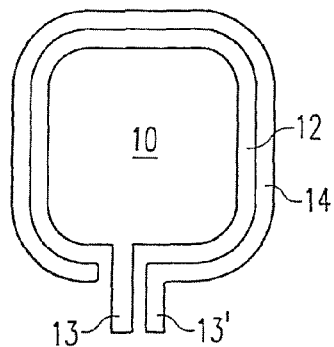
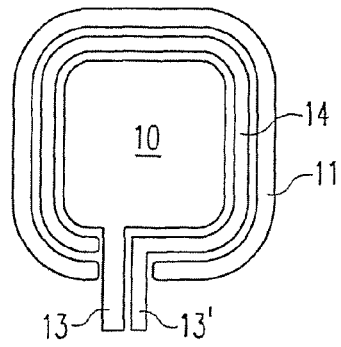
Fig. 3
Fig. 4
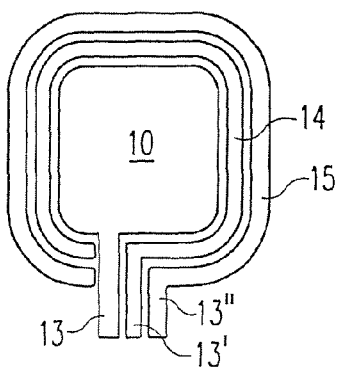
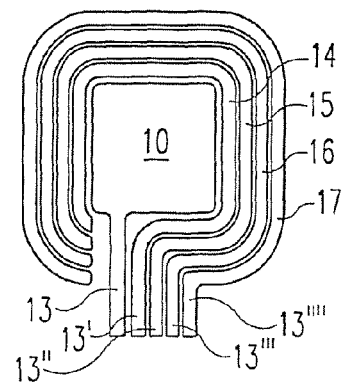
Fig. 5
Fig. 6

ELECTRODE DEVICE

FIELD OF THE INVENTION

The disclosed embodiments relate to an electrode device, in particular a neutral electrode for introducing a high frequency treatment current while monitoring the contact of the electrode to the skin surface and the high frequency current flow and its spatial distribution such that increased safety is ensured.

BACKGROUND

Monopolar instruments, wherein the treatment current is introduced into the tissue via a neutral electrode and flows through the body, are used, amongst other things, during electrosurgical interventions. Such an arrangement is illustrated in FIGS. 1 and 2. The instrument comprises a generator 1, which supplies a high frequency electrical current (normally 350 kHz), to which an electrosurgical instrument 2 and a neutral electrode 3 are connected. Neutral electrode 3 is affixed with an intermediate layer of a conductive gel to a skin layer of a patient to be treated.

EP 1 173 095 B1 discloses a neutral electrode which has a construction corresponding to that according to FIGS. 1 and 2. Neutral electrode 3 has a backing foil 9 to which is attached a main electrode 10 that may be connected to generator 1 via a terminal lug 13. An electrically conductive ring 11 is provided around main electrode 10 and is separated from main electrode 10 by a gap 12. The electrically conductive ring 11 leads to an improved current distribution on the skin section contacted or on the tissue situated beneath it. It should be noted that the various types of tissue have very different specific resistances. For example, muscles have a specific resistance of 0.2 m$\Omega$cm (at 1 MHz), whereas the specific resistance of blood is 0.16 m$\Omega$cm and that of fat is 3.3 m$\Omega$cm. Furthermore, the affixed neutral electrodes may also easily become detached, especially around the edges such that contact is interrupted in places.

Many suggestions have been made to determine correct seating of the electrode. For example, in EP 0 390 937 B1 a device for monitoring the application of neutral electrodes during high frequency surgery is proposed wherein work is carried out using two electrodes of equal size and a differential resistance is measured between the two electrodes. Correct or faulty seating of the electrode is deduced from the measured result.

EP 1 051 949 B1 discloses a neutral electrode with an impedance measuring device, however, it is not possible to infer precise directions for the construction of such an electrode from this printed publication.

In all cases, known electrode construction and methods are only suitable to a limited degree for ensuring correct introduction of a high frequency treatment current by way of a neutral electrode with justifiable expenditure.

Thus, the object of the disclosed embodiments is to provide an electrode device and a method for monitoring the contact and the high frequency current flow and its spatial distribution such that increased safety is ensured due to improved current introduction properties.

SUMMARY

Disclosed embodiments include an electrode device, in particular a neutral electrode for introducing a high frequency treatment current via a skin section of a human or animal body (e.g., during a monopolar electrosurgical treatment) including at least one main electrode for introducing the treatment current into the body, an impedance measuring device for measuring an impedance between the main electrode and the body or an auxiliary electrode, an evaluation device connected to the impedance measuring device for generating an evaluation signal relating to the impedance and/or at least a possible heating of the body and/or of the skin section, at least one measuring electrode disposed at a distance from the main electrode and the impedance measuring device also includes at least one measuring current generator that is connected to the main electrode and to the measuring electrode for the generation of a high frequency measuring current, which flows between said measuring electrode and the main electrode.

In disclosed embodiments a separate measuring electrode is provided and a separate measuring current (independent of the actual treatment current) is used in order to measure the impedance between the measuring electrode and the main electrode. Thus, practically, only the measuring current flows between the generator and the measuring electrode. If the impedance rises, this is a sign that at least a portion of the electrode surface has lost contact with the skin section lying beneath it. Since such a loss of contact accompanies an increased current density regarding the treatment current, this measurement also simultaneously determines whether heating of the skin or tissue sections lying beneath the electrode is to be anticipated.

The measuring current preferably has a frequency or phase position which differs from the treatment current such that the measuring current is separable from the treatment current by means of filter devices. In this case the measuring current is also a high frequency current such as is required by the regulations relating to electrosurgical equipment. Since both the measuring current and the treatment current are defined by the corresponding circuitry parts, it is possible to construct very narrow band filters (e.g., by means of a PLL circuit) such that very accurate measurements are to be expected.

The frequency of the measuring current is preferably lower than the frequency of the treatment current. Thus the measuring current does not come into the frequency range of harmonics, which are generated for example by the occurrence of arcs during electrosurgery.

The impedance measuring device preferably has a voltage measuring device for measuring a voltage drop between the main electrode and the measuring electrode on transmission of the measuring current. Thus, the generator for producing the measuring current only needs to be designed as an alternating current source with constant amplitude, which is easy to put into practice in terms of circuitry.

Furthermore, the impedance measuring device preferably has a voltage measuring device for measuring a voltage drop between the main electrode and the measuring electrode when the measuring current is flowing. Thus measured values, which have an informative value with respect to anticipating heating of the tissue or skin section, can be generated in a simple manner.

The measuring electrode is (or the plurality of measuring electrodes are) preferably designed as an electrically conductive ring, thus simultaneously taking over the function, already described above and known from the prior art according to EP 1 173 095 B1, of reducing the current density and thus decreasing heating of the tissue.

A preferred embodiment provides a plurality of measuring electrodes (e.g., electrically conductive rings) and a plurality of impedance measuring devices. The evaluation device is designed such that it is possible to identify a curve of the voltage drops in the treatment current between the main electrode and the measuring electrodes. With such an arrangement, it is possible to detect an inhomogeneity in the tissue based on its specific resistance beneath the electrode device. Furthermore, using such an arrangement makes it easy to detect detachment of the electrode device.

The evaluation device is preferably designed in such a manner that a warning signal is emitted if a voltage drop to the measuring electrode caused by the treatment current exceeds a predetermined threshold, as a function of $R_{UEB}$. This further increases the electrode device's safety.

BRIEF DESCRIPTION OF THE DRAWINGS

In the following, the disclosed embodiments will now be described in more detail with reference to an exemplary embodiment, which will be explained in more detail with reference to the enclosed drawings.

FIG. 1 illustrates a view from above onto a known electrode device.

FIG. 2 illustrates a cross-sectional view of the electrode device according to FIG. 1 along the line II-II.

FIG. 3 illustrates a view from above onto a first disclosed embodiment.

FIG. 4 illustrates a disclosed second embodiment.

FIG. 5 illustrates a third disclosed embodiment.

FIG. 6 illustrates a fourth disclosed embodiment.

FIG. 9 illustrates a representation corresponding to that of FIG. 8 with resistance conditions additionally drawn in.

FIG. 10 illustrates a cross-sectional view of a disclosed embodiment according to FIG. 3 with associated peripheral components drawn in.

DETAILED DESCRIPTION

Figure 7:
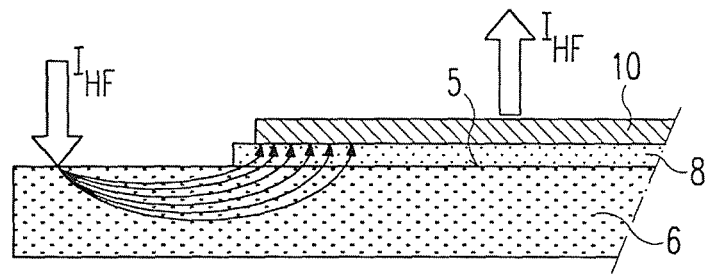
FIG. 7 illustrates a partial section through a main electrode and the tissue lying beneath it in a symbolic representation.
Figure 7:
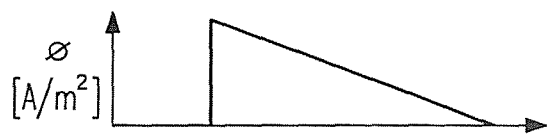

The same reference numerals are used in the following description for identical parts and parts acting in an identical manner.

In the embodiment illustrated in FIG. 3, a main electrode 10 is provided in the center of the electrode arrangement. An electrically conductive ring is provided which is separated by a gap 12 from main electrode 10. In this embodiment, the electrically conductive ring 11 forms a measuring electrode 14. The electrically conductive ring (measuring electrode 14) surrounds main electrode 10 on one hand and on the other extends by means of a finger (still being divided by a gap 12) into main electrode 10. Main electrode 10 includes a terminal lug 13. Measuring electrode 14 is connected to the electric circuit via a terminal lug 13' (as described below).

FIG. 4 illustrates an additional embodiment. The embodiment according to FIG. 4 differs from that according to FIG. 3 in that an electrically conductive ring 11 is provided in addition to the measuring electrode 14 and surrounds main electrode 10 and measuring electrode 14 (separated by a gap). Terminal lug 13' is provided on the measuring electrode 14, thus electrically conductive ring 11 has no terminal lug.

FIG. 5 illustrates an additional embodiment. The embodiment according to FIG. 5 differs from that according to FIG. 4 in that electrically conductive ring 11 is now designed as an additional measuring electrode 15, thus it has terminal lug 13", via which a connection may be made to peripheral components.

FIG. 6 illustrates an additional embodiment. The embodiment according to FIG. 6 differs from that according to FIG. 5 in that a total of four measuring electrodes 14, 15, 16 and 17 are provided, each of which surrounds the main electrode 10 at ever-increasing distances and are each separated from the main electrode 10 and from each other by gaps.

Figure 8:
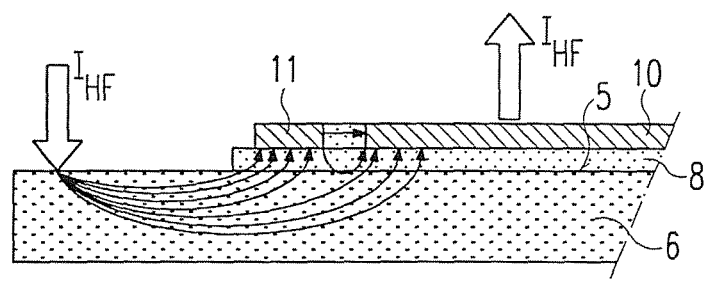
FIG. 8 illustrates a representation corresponding to that of FIG. 7, but with an additional equipotential electrode.
Figure 8:
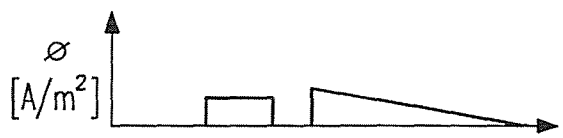
Figure 9:
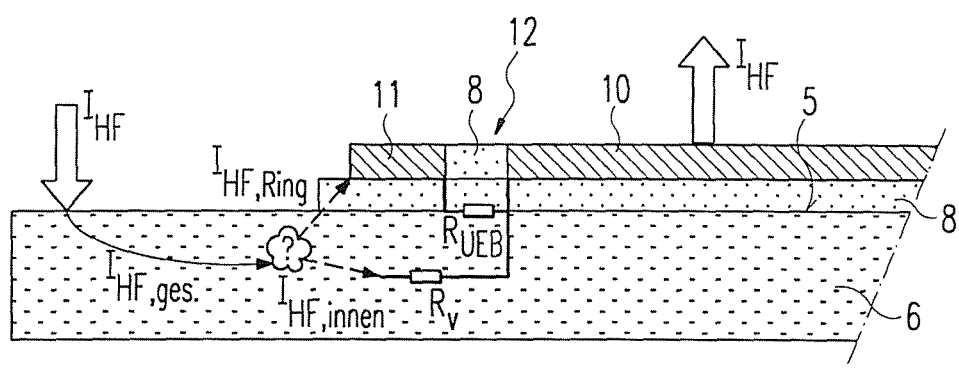

Referring now to FIGS. 7-9, the problem existing with known arrangements is explained in greater detail.

A "simple" arrangement, includes only a single main electrode 10 is affixed to a skin section 5 by way of a conductive gel 8. A treatment current $I_{HF}$ flows from the surgical instrument (not illustrated here) into tissue 6 of the patient to be treated. The current continues to flow in tissue 6 and through skin section 5 by way of conductive gel 8 into main electrode 10 and from there to the corresponding opposite pole of the high frequency generator used (not illustrated). Treatment current $I_{HF}$ will always choose the shortest path, such that the current density is highest at that section of main electrode 10 which is closest to the treatment point (e.g., where the treatment current flows into tissue 6). Moreover, current concentration takes place at the edges of main electrode 10. This is represented schematically in FIG. 7 in the diagram shown below the sectional drawing.

The arrangement shown in FIG. 8 differs from that according to FIG. 7 by an electrically conductive ring 11 provided therein (such as is illustrated in FIG. 1). Due to the existing resistance conditions, which are shown in FIG. 9 in a simplified form, electrically conductive ring 11 brings about a "relief" of the tissue, meaning that part of the treatment current flows into electrically conductive ring 11 and (by way of conductive gel 8 amongst other things) from there gets into main electrode 10. This results in a reduction of the current density at any particular portion of tissue 6, such as is indicated schematically in the diagram in FIG. 8.

Figure 10:
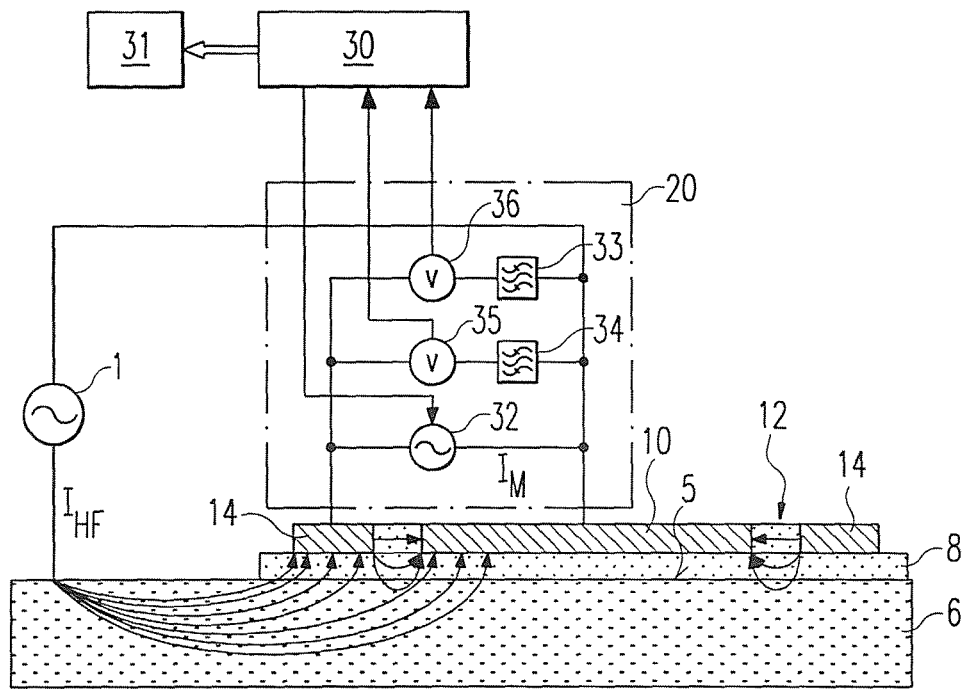

In the embodiment illustrated in FIG. 10, the arrangement is similar to that according to FIG. 9, however the electrically conductive ring provided in FIG. 9 forms a first measuring electrode 14 in the embodiment of FIG. 10 (such as is illustrated in FIG. 3).

Impedance measuring device 20 includes a measuring current generator 32, the outputs of which are connected to main electrode 10 and to measuring electrode 14. Measuring current generator 32 delivers a constant measuring current $I_M$, the frequency of which is lower than that of the treatment current $I_{HF}$. For example, if the frequency of the treatment current $I_{HF}$ is 350 kHz then a frequency of approximately 70 kHz would be appropriate for the measuring current $I_M$. Measuring current generator 32 may be controlled by an evaluation device 30 by way of a corresponding control cable.

A voltage measuring device 35 (upstream of which is connected a filter 34) is provided parallel to measuring current generator 32. Filter 34 is matched in its conducting-state frequency to the frequency of measuring current $I_M$ such that voltage measuring device 35 merely reflects the amplitude of the voltage fractions which arises due to the drop in measuring current $I_M$ across the measuring path between main electrode 10 and measuring electrode 14 when measuring current $I_M$ flows. A corresponding measuring voltage signal is supplied to evaluation device 30.

Furthermore, impedance measuring device 20 contains a second voltage measuring device 36 with a series-connected filter 33, the conducting-state frequency of which is matched to the frequency (350 kHz) of treatment current $I_{HF}$. The output signal of the second voltage measuring device 36, which is supplied to evaluation device 30, reflects the voltage drop which arises due to the treatment current $I_{HF}$ flowing between measuring electrode 14 and main electrode 10.

Evaluation device 30 is connected to a display or signal generating device 31.

In operation, after affixing the electrode device to a skin section 5 of a patient, a measuring current $I_M$ is produced continuously or intermittently by generator 32. The voltage measured by voltage measuring device 35 thus expresses (with constant measuring current $I_M$) a measure for the impedance which is present between measuring electrode 14 and main electrode 10. If the impedance rises in relation to a predefinable "standard value" (or a standard value ascertained from earlier investigations) then it may be assumed from this that the resistance between measuring electrode 14 and tissue 6 and/or the resistance between main electrode 10 and tissue 6 is very high or has risen. In turn, it can be identified from this that there is a contact failure; thus the electrode has become detached or too high a resistance exists between main electrode 10 and/or measuring electrode 14 and skin section 5 or tissue 6 lying beneath it for other reasons. Accordingly, an appropriate display is output on the display or signal generation device 31 via evaluation device 30 to warn the operating staff that there is now a risk of too high a current density and thus excessive heating of the tissue 6 or skin section 5.

If a voltage drop, which exceeds a predetermined threshold, continues to be determined via second voltage measuring device 36 when a treatment current $I_{HF}$ is flowing, then it may in turn be concluded from this that incorrect resistance conditions exist. It is also possible to infer too high a current density from this and thus a risk of excessive heating.

Figure 11:
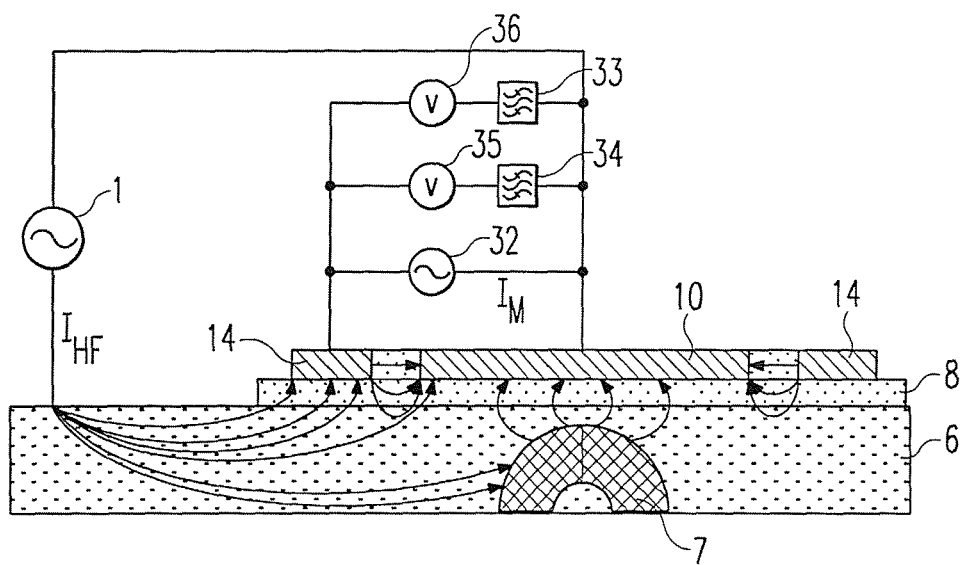
FIG. 11 illustrates a representation corresponding to that of FIG. 10, but with other conditions in the tissue.

Referring to FIG. 11, it is illustrated how an additional problem may be detected using the disclosed embodiments. If a vessel 7 runs closely underneath electrode 10 or associated skin section 5, or if tissue 6 contains a relatively large amount of fat, then due to the inhomogeneous resistance conditions present, an increased current flow arises between the region of vessel 7 and main electrode 10. This causes a reduced current flow between measuring electrode 14 (acting as an electrically conductive ring) and main electrode 10, which is detected by second voltage measuring device 36 and is "communicated" by evaluation device 30. In this case, a signal may be output by way of display or signal generation device 31 which alerts the operating staff that, due to the existing resistance conditions, a regionally increased current density is to be expected. As is generally known, this may lead to excessive heating of tissue 6 or of the skin lying beneath main electrode 10.

Figure 12:
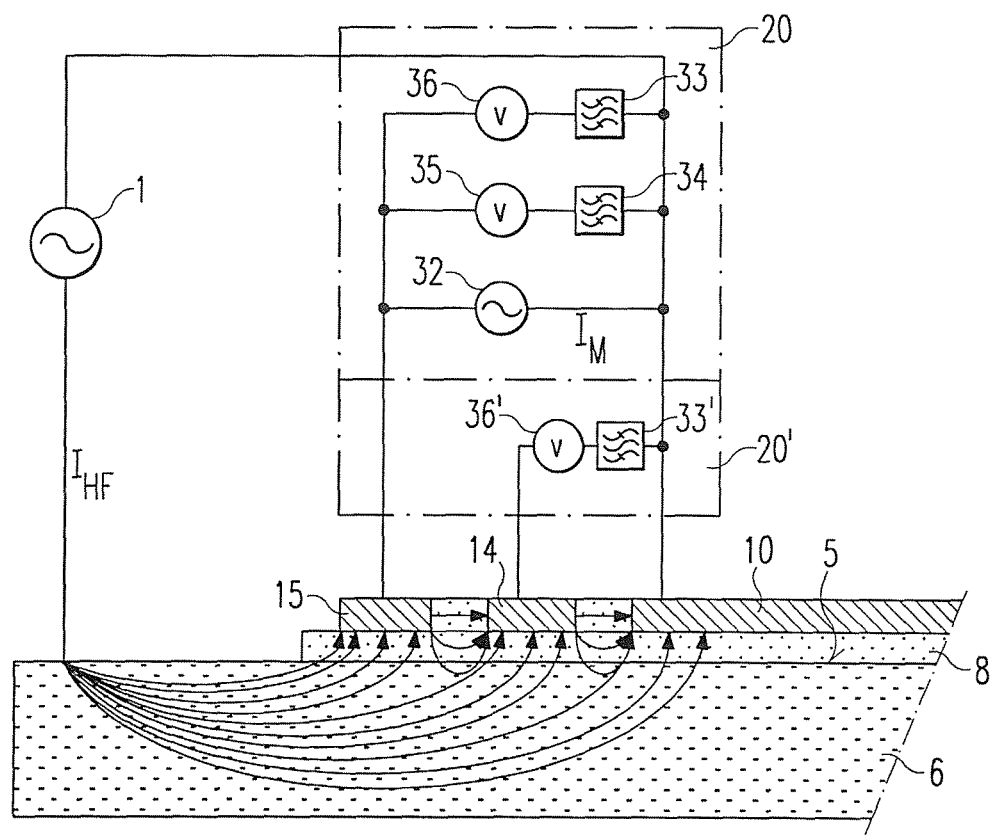
FIG. 12 illustrates a representation corresponding to that of FIG. 10, with an additional electrically conductive ring.

In the embodiment illustrated in FIG. 12, a plurality of measuring electrodes 14, are provided (such as is illustrated in FIG. 5). Furthermore, a plurality of second voltage measuring devices 36, 36' are provided such that a curve of the voltage drop is detectable when a treatment current $I_{HF}$ flows between main electrode 10 and each of first measuring electrode 14 and second measuring electrode 15. Having a plurality of measuring electrodes 14, 15 and a plurality of second voltage measuring devices 36, 36' allows for easier detection of whether inhomogeneities are present in tissue 6 or in the entire current path between generator 1 and main electrode 10 (based on the curve of the voltage drop). Furthermore, detachment of the electrode device at the edges can also be detected even more easily, more accurately and its significance is easier to estimate. If, for example, the voltage drop between measuring electrode 14 and 15 signals a detachment, but if there is still a correct value between main electrode 10 and measuring electrode 14, then it is possible to conclude from this that there is still no "risk" for the patient but that correct attachment of the neutral electrode should be checked at this point.

The evaluation circuitry can determine the following parameters:

$I_M$ Measuring current for measuring contact resistance $R_{UEB}$ $U_{M,\,ring}$ Voltage drop due to $I_M$ between electrically conductive ring and inner surface, is used for calculating the contact resistance in conjunction with $I_M$.

$U_{HF,\,ring}$ High frequency voltage (350 kHz) between main electrode and electrically conductive ring. Together with the contact resistance, a measure for the current which flows "across" the electrically conductive ring.

$I_{HF}$ total current, which flows via the neutral electrode to the generator $$R_{UEB} = \frac{U_{M,Ring}}{I_M}$$

$$P_{HF,innen} = (I_{HF} - I_{HF,Ring})^2 * \left(R_{UEB} * \frac{I_{HF,Ring}}{I_{HF} - I_{HF,Ring}}\right)$$

$$= R_V * (I_{HF} - I_{HF,Ring})^2$$

$$R_V = \frac{I_{HF,Ring}}{I_{HF} - I_{HF,Ring}} * R_{UEB}$$

$$P_{HF,ring} = U_{HF,ring} * I_{HF,ring} = \frac{U_{HF,Ring}^2}{R_{UEB}}$$

$R_{UEB}$ Contact resistance for determining the quality of contact and calculation of the current distributed across the ring $I_{HF,\,ring}$ High frequency current which flows in the electrically conductive ring and is distributed $P_{HF,\,internal}$ Output which is converted into heat at the edge of the main electrode $P_{HF,\,ring}$ Output which is converted into heat in the electrically conductive ring $R_V$ Virtual resistance of the tissue underneath the neutral electrode across which that part of the high frequency current flows which is not distributed across the ring. Serves as an auxiliary variable for output calculation.

From the two calculated outputs $P_{HF,\,internal}$ and $P_{HF,\,ring}$, it is possible to estimate the temperature increase at the edges of the neutral electrode as these outputs are converted in a geometrically approximately known region. It is possible to make such a general assumption of the thermal conductivity of the tissue lying beneath the neutral electrode since on one hand the affected area is very restricted from the point of view of its proportions and on the other no direct air flows or other external influences can occur underneath the electrode.

Thus, the disclosed embodiments enable better detection of detachment of the electrode device around the edges. Detachment from the skin is detected with the same accuracy on every edge of the neutral electrode. Precise monitoring is necessary here since the highest current density also occurs in the edge region. In contrast, with known electrodes, the detection of these important parameters is less accurate perpendicular to the gel bridge than parallel to it. This disadvantage is particularly significant in the commercially available divided neutral electrodes (see, for example, EP 0 390 937 B1).

By measuring the high frequency voltage between the electrically conductive ring and the main electrode, the current (which is distributed by the electrically conductive ring) can be determined by means of the known contact resistance. Thus it is possible to make a statement about the ratio of total current to current across the electrically conductive ring and thus the effectiveness of the distribution effect of the electrically conductive ring can be determined.

It is also possible to draw conclusions about the resistance conditions of the deeper, current-conducting tissue layers by measuring the current distribution between the tissue underneath the ring and the electrically conductive ring.

If tissue with very good conductivity and having a low proportion of area is located underneath the area of the neutral electrode discharging treatment current $I_{HF}$, e.g. a large blood vessel closely below the skin surface (possibly surrounded by adipose tissue), then a large part of the current will flow across it which, due to the small area, may lead to high current densities and thus to burns at these points. Such cases are known from the past. With the arrangement described or the method described, this problem may be detected since only a small proportion of treatment current $I_{HF}$ will flow across the electrically conductive ring. Consequently, the remaining treatment current must be able to get under the main electrode on a path with lower conductivity.

It is possible to calculate the associated heat loss using the known current and resistance conditions. Thus it is possible to make a statement about a possible temperature increase in the edge region of the electrode where the temperature increase is also highest. Although the exact thermal behaviour of the tissue differs from case to case, because one is dealing with a geometrically very restricted region underneath the electrode, it is highly probable that an inadmissible temperature increase can be estimated with a good level of accuracy.

The orientation of the electrode according to the disclosed embodiments in relation to the operating field is virtually meaningless (apart from the terminal lug). There is no longer any possibility of an asymmetrical treatment current $I_{HF}$ occurring as there is only one single area (main electrode 10) conducting the treatment current. Thus any possible errors due to a neutral electrode that is not aligned correctly with the operating field are also prevented.

It should be pointed out here that all the above described parts and in particular the details illustrated in the drawings are essential for the disclosed embodiments alone and in combination. Adaptations thereof are the common practice of persons skilled in the art.

The invention claimed is:

1. A neutral electrode device for introducing a high frequency treatment current via a skin section of a human or animal body comprising:
   at least one main electrode for introducing the treatment current into the body;
   an impedance measuring device for measuring an impedance between the main electrode and the body and for generating an impedance signal;
   an evaluation device connected to the impedance measuring device for generating an evaluation signal relating to the impedance and/or relating to possible heating of the body and/or of the skin section; and
   at least one measuring electrode disposed at a distance from the main electrode;
   wherein the impedance measuring device comprises at least one measuring current generator connected to the main electrode and the measuring electrode for the generation of a high frequency measuring current which flows between the measuring electrode and the main electrode,
   wherein the measuring current has a frequency or phase position which differs from that of the treatment current such that the measuring current is separable from the treatment current by means of filter devices,
   wherein the impedance measuring device comprises a voltage measuring device for measuring a voltage drop between the main electrode and the measuring electrode on the basis of the measuring current being transmitted between the measuring electrode and the main electrode, and
   wherein the impedance measuring device comprises a voltage measuring device for measuring a voltage drop between the main electrode and the measuring electrode on the basis of a flowing treatment current.

2. The electrode device according to claim 1, wherein the frequency of the measuring current is lower than the frequency of the treatment current.

3. The electrode device according to claim 1, wherein an edge of the measuring electrode is disposed around an edge of the main electrode with an equidistant gap.

4. The electrode device according to claim 1, wherein the measuring electrode is an electrically conductive ring.

5. The electrode device according to claim 1, wherein a plurality of measuring electrodes each forming electrically conductive rings and a plurality of impedance measuring devices are provided and the evaluation device determines a curve of the voltage drops of the treatment current from the main electrode to the measuring electrodes.

6. The electrode device according to claim 1, wherein the evaluation device causes a warning signal to be emitted if a voltage drop to the measuring electrode caused by the treatment current exceeds a predetermined threshold.

7. A method of detecting decreased contact of a main electrode of an electrode device used for introducing a high frequency treatment current via a skin section of a human or animal body, the electrode device comprising at least one main electrode for introducing the treatment current into the body and at least one measuring electrode disposed at a distance from the main electrode, the method comprising the steps of:
   conducting a high frequency measuring current for measuring an impedance between the main electrode and the body;
   evaluating the impedance in order to detect the decreased contact of the electrode with the skin section;
   separating a frequency of the treatment current from a frequency of the measuring current by filters;
   measuring a voltage drop between the main electrode and the measuring electrode on the basis of the measuring current being transmitted between the measuring electrode and the main electrode; and
   measuring a voltage drop between the main electrode and the measuring electrode on the basis of a flowing treatment current.

8. The method of claim 7, wherein the frequency of the treatment current is higher than the frequency of the measuring current.

9. The method of claim 7, wherein the electrode device further comprises a plurality of measuring electrodes, each of which is an electrically conductive ring, and wherein the method further comprises detecting a curve of the voltage drops of the treatment current from the main electrode to the measuring electrodes.

10. The method of claim 7, further comprising generating a warning signal if a voltage drop to the measuring electrode caused by the treatment current exceeds a predetermined threshold.

11. The electrode device of claim 1, wherein the device is for use during a monopolar electrosurgical treatment.

12. The electrode device of claim 1, wherein the at least one measuring current generator is a part of the impedance measuring device.

13. A method of detecting heating of a skin section of a human or animal body caused by an electrode device used for introducing a high frequency treatment current via the skin section, the electrode device comprising at least one main electrode for introducing the treatment current into the body and at least one measuring electrode disposed at a distance from the main electrode, the method comprising the steps of:
- conducting a high frequency measuring current for measuring an impedance between the main electrode and the body;
- evaluating the impedance in order to detect the heating of the skin;
- separating a frequency of the treatment current from a frequency of the measuring current by filters;
- measuring a voltage drop between the main electrode and the measuring electrode on the basis of the measuring current being transmitted between the measuring electrode and the main electrode; and
- measuring a voltage drop between the main electrode and the measuring electrode on the basis of a flowing treatment current.

* * * * *

UNITED STATES PATENT AND TRADEMARK OFFICE
CERTIFICATE OF CORRECTION

PATENT NO. : 8,449,536 B2  
APPLICATION NO. : 12/374265  
DATED : May 28, 2013  
INVENTOR(S) : Peter Selig Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 808 days.

Signed and Sealed this
Eighth Day of September, 2015

Michelle K. Lee
*Director of the United States Patent and Trademark Office*